US012423616B2

(12) United States Patent
Gorla et al.

(10) Patent No.: US 12,423,616 B2
(45) Date of Patent: Sep. 23, 2025

(54) METHODS AND SYSTEMS FOR AUTOMATICALLY TUNING WEIGHTS ASSOCIATED WITH BREEDING MODELS

(71) Applicant: Monsanto Technology LLC, St. Louis, MO (US)

(72) Inventors: Viveka Gorla, Chesterfield, MO (US); TingYu Ho, Seattle, WA (US); Adam David Scott, Maryland Heights, MO (US); Aviral Shukla, Defiance, MO (US); Yiduo Zhan, Chesterfield, MO (US); Zihao Zhao, Woodinville, WA (US)

(73) Assignee: Monsanto Technology LLC, Saint Louis, MO (US)

( * ) Notice: Subject to any disclaimer, the term of this patent is extended or adjusted under 35 U.S.C. 154(b) by 966 days.

(21) Appl. No.: 17/540,025

(22) Filed: Dec. 1, 2021

(65) Prior Publication Data

US 2022/0172120 A1    Jun. 2, 2022

Related U.S. Application Data

(60) Provisional application No. 63/120,662, filed on Dec. 2, 2020.

(51) Int. Cl.
*G06N 20/00*    (2019.01)
(52) U.S. Cl.
CPC .................................. *G06N 20/00* (2019.01)
(58) Field of Classification Search
CPC ................................................ G06N 20/00
USPC ......................................................... 703/11
See application file for complete search history.

(56) References Cited

U.S. PATENT DOCUMENTS

| 10,327,400 | B2 | 6/2019 | Chavali et al. |
| 2008/0163824 | A1 | 7/2008 | Moser et al. |
| 2010/0076911 | A1 | 3/2010 | Xu et al. |
| 2012/0123980 | A1 | 5/2012 | Bhandari et al. |

(Continued)

FOREIGN PATENT DOCUMENTS

| CN | 104112233 A | 10/2014 | ............. G06Q 50/02 |
| CN | 109378036 A | 2/2019 | ............. G16B 20/00 |

(Continued)

OTHER PUBLICATIONS

"Simulation Modeling in Plant Breeding: Principles and Applications" Published by Elsevier (Year: 2007).*

(Continued)

*Primary Examiner* — Zeina Elchanti
(74) *Attorney, Agent, or Firm* — Harness, Dickey & Pierce, P.L.C.

(57) ABSTRACT

Systems and methods for use in identifying weights to be employed in a selection algorithm associated with plant advancement are disclosed. One example method includes identifying a start set of weights for a selection algorithm associated with a breeding program, and for each scale parameter value in a schedule, and for each of N iterations, modifying the start set of weights based on the scale parameter value, identifying a set of germplasm based on at least the modified set of weights, advancing the modified set of weights to a next iteration as the start set of weights when certain criteria are satisfied, and identifying the modified set of weights as an output when the iteration is equal to N.

20 Claims, 5 Drawing Sheets

(56) References Cited

U.S. PATENT DOCUMENTS

| | | | |
|---|---|---|---|
| 2012/0144508 A1 | 6/2012 | Hayes et al. | |
| 2016/0007130 A1* | 1/2016 | Germain | H04R 3/00 381/58 |
| 2017/0354105 A1* | 12/2017 | Polavarapu | A01H 1/02 |
| 2019/0174691 A1 | 6/2019 | Chavali et al. | C12Q 1/6827 |
| 2019/0180845 A1 | 6/2019 | Chavali et al. | |
| 2023/0292687 A1* | 9/2023 | Mockler | A01H 6/4666 800/260 |

FOREIGN PATENT DOCUMENTS

| | | | |
|---|---|---|---|
| CN | 111465320 A | 7/2020 | A01H 1/02 |
| CN | 111627495 A | 9/2020 | G16B 20/20 |

OTHER PUBLICATIONS

Hassanzadeh, H. R., & Rouhani, M. (Jul. 2010). A multi-objective gravitational search algorithm. In Computational Intelligence, Communication Systems and Networks (CICSyN), 2010 Second International Conference on (pp. 7-12). IEEE.

Censor, Y. (1977). Pareto optimality in multiobjective problems. *Applied Mathematics and Optimization*, 4(1), 41-59.

Kim, I. Y., & De Weck, O. L. (2006). Adaptive weighted sum method for multiobjective optimization: a new method for Pareto front generation. *Structural and multidisciplinary optimization*, 31(2), 105-116.

Jiang, S., Cai, Z., Zhang, J., & Ong, Y. S. (Jul. 2011). Multiobjective optimization by decomposition with Pareto-adaptive weight vectors. *In Natural Computation (ICNC), 2011 Seventh International Conference on* (vol. 3, pp. 1260-1264). IEEE.

Zhang, K. S., Han, Z. H., Li, W. J., & Song, W. P. (2008). Bilevel adaptive weighted sum method for multidisciplinary multi-objective optimization. *AIAA journal*, 46(10), 2611-2622.

Azodi et al., "Benchmarking Parametric and Machine Learning Models for Genomic Prediction of Complex Traits" In: G3 Genes|Genomes|Genetics, vol. 9, Issue 11, (Nov. 1, 2019) (23 pgs.).

CN2021800806961: Chinese Office Action dated Nov. 29, 2024. CN2021800806961 has the same priority claim as the instant application.

* cited by examiner

METHODS AND SYSTEMS FOR AUTOMATICALLY TUNING WEIGHTS ASSOCIATED WITH BREEDING MODELS

CROSS-REFERENCE TO RELATED APPLICATION

This application claims the benefit of, and priority to, U.S. Provisional Application No. 63/120,662, filed on Dec. 2, 2020. The entire disclosure of the above application is incorporated herein by reference.

FIELD

The present disclosure generally relates to methods and systems for use in or with agricultural selection models and, in particular, to methods and systems for automatically tuning weights associated with such models for use in identifying and/or selecting desired parents for subsequent use (e.g., for advancement in breeding pipelines, etc.).

BACKGROUND

This section provides background information related to the present disclosure which is not necessarily prior art.

In plant development, modifications can be made in plants either through selective breeding or genetic manipulation. And, when a desirable improvement is achieved, a commercial quantity is developed by planting seeds from selected ones of the plants and harvesting resulting seeds over several generations. In connection with selective breeding, numerous decisions are made based on characteristics and/or traits of the plants being bred, and similarly on characteristics and/or traits of their parents. And, not all resulting crosses are guaranteed to inherit or exhibit the desired traits. As such, as part of selecting particular plants for further development following such modifications, samples are taken from the plants and/or their resulting seeds and tested so that only plants and/or seeds having the desired characteristics and/or traits are advanced. That said, plant development involves large numbers of possible crosses, from which final breeding decisions must be made.

DRAWINGS

The drawings described herein are for illustrative purposes only of selected embodiments, are not all possible implementations, and are not intended to limit the scope of the present disclosure.

DETAILED DESCRIPTION

Example embodiments will now be described more fully with reference to the accompanying drawings. The description and specific examples included herein are intended for purposes of illustration only and are not intended to limit the scope of the present disclosure.

Various breeding techniques are commonly employed in agricultural industries to produce desired offspring. Often, breeding programs implement such techniques to obtain offspring having desired characteristics or combinations of characteristics (e.g., yield, disease resistance, etc.). However, it is difficult to accurately determine the best parents to cross when selecting a set of breeding starts, or germplasm, for such programs, especially when a large number of options are available. Uniquely, the systems and methods herein are configured to select parents for use in breeding pipelines based on weighted values associated with predicted commercial values of potential crosses between the parents, relatedness and/or risks associated with the given crosses, and individual traits and/or characteristics of the parents (and/or the parents' parents, and/or other members in the parental lines). What's more, rather than relying on manual formulation of the weighting between the different parameters, the systems and methods herein identify overlap between the selected parents and the parents selected by human breeders whereby enhanced decision making is provided. In this manner, a more complete picture of the potential crosses of the parents is provided, from which efficiency in selecting populations of crosses for the plant breeding pipelines can be gained.

Figure 1:
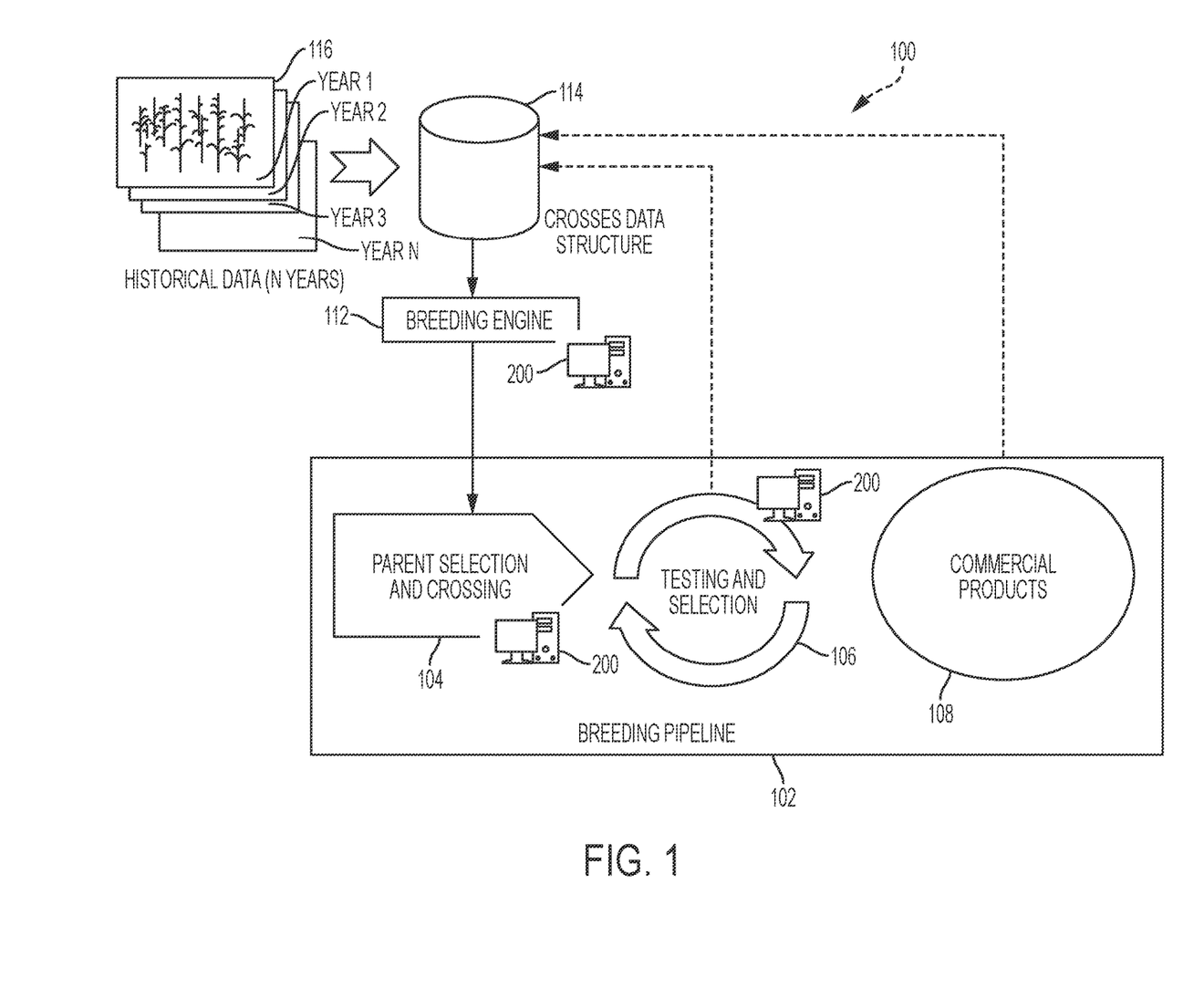
FIG. 1 illustrates an example system of the present disclosure suitable for use in identifying and/or selecting parents for use in plant breeding and/or for advancement in plant breeding pipelines.

With reference now to the drawings, FIG. 1 illustrates an example system 100 for identifying crosses for use in breeding plants, in which one or more aspects of the present disclosure may be implemented. Although, in the described embodiment, parts of the system 100 are presented in one arrangement, other embodiments may include the same or different parts arranged otherwise depending, for example, on particular plants being bred, particular characteristics and/or traits of interest, particular breeding techniques implemented, etc.

As shown in FIG. 1, the system 100 generally includes a breeding pipeline 102, which is provided to create new plants by crossing an existing pool of parents, or germplasm, including origins, progenies, and/or hybrids, etc. In certain embodiments, the breeding pipeline 102 is employed to create commercial products by first crossing parent plants to produce offspring seed (and/or plants). The pipeline 102 generally defines a pyramidal progression, whereby it starts with a large number of potential crosses from parents, and keeps narrowing down to pick preferred and/or desired ones of the crosses for commercialization. The pipeline 102 often involves identification of preferred performing populations from this large number of potential crosses, which typically involves subjecting the populations of offspring to rigorous testing using a wide range of methods known in the art. In certain breeding pipelines (e.g., large industrial breeding pipelines, etc.), this process may involve testing hundreds, thousands, or more crosses in multiple phases at several locations, over several years, to arrive at a reduced set of crosses selected for commercial product development. In short, the breeding pipeline 102 comprises many processes designed to reduce a large number of crosses down to a relatively few number of superior-performing commercial products.

As shown in FIG. 1, the breeding pipeline 102 includes a parent selection and crossing phase 104 and a testing and selection phase 106, which together yield one or more commercial products 108 (broadly, selected crosses). In general, the pipeline 102 includes a variety of conventional processes known to those skilled in the art, as described below, used in the different phases 104, 106 to ultimately achieve the commercial products 108. As will be described in more detail hereinafter, the illustrated system 100 includes a breeding engine 112 uniquely configured, in connection with a crosses data structure 114, to make and provide the selection of parents to the breeding pipeline 102, and in particular to the parent selection and crossing phase 104 thereof (thereby facilitating an improved likelihood of providing successful commercial products 108, and potentially utilizing fewer parents/crosses in phase 104 than in traditional operations). Once the existing pool of parents, or germplasm, is identified, created, etc., it is directed to the testing and selection phase 106, which includes a growing space, such as, for example, a greenhouse, a nursery, a breeding plot, a field, etc. In connection therewith, one or more of the germplasm (from phase 104) are then planted in, or more generally subject to, the growing space in phase 106, whereupon plants are grown (as derived from the one or more germplasm). In connection therewith, the disclosure of U.S. Pat. No. 10,327,400 (Title: Methods for Identifying Crosses for use in Plant Breeding) and the disclosures of U.S. Patent Publ. No. 2019/0180845 (Title: Methods and Systems for Identifying Progenies for use in Plant Breeding) and U.S. Patent Publ. No. 2019/0174691 (Title: Methods and Systems for Identifying Hybrids for use in Plant Breeding) are all incorporated herein by reference in their entireties.

The breeding engine 112 is configured to employ an algorithm (e.g., a plant selection model, an agricultural selection model, etc.) to select germplasm (e.g., origins, progenies, and/or hybrids, etc.) for advancement in the breeding pipeline 102. One example algorithm is provided below as Equation (1). Equation (1), in short, relates to a multi-objective selection process, providing a weighted sum of the objectives of plant performance, risk, and diversity simultaneously.

$$f(\lambda, x) = \left( \lambda_p \sum_{i=1}^{nN} x_i p_i - \lambda_r \sum_{i=1}^{nN} x_i r_i - \lambda_{d_1} 1^S \theta - \lambda_{d_2} 1^S \varphi - \lambda_{d_3} 1^S \gamma \right) \quad (1)$$

In Equation (1), different settings of the weight factors, $\lambda$, will lead to different results of the function $f(\lambda, x)$. The breeding engine 112 is further configured, herein, to select the weights (or weight factors) to be included in Equation (1) to achieve one or more objectives associated with the selection of germplasm, such as origins, progenies, and/or hybrids, etc. In particular, in this example embodiment, the breeding engine 112 is configured to initiate with a start set of weights (or weight factors) for Equation (1), for example, $\lambda_p$, $\lambda_r$, $\lambda_{d1}$, $\lambda_{d2}$, and $\lambda_{d3}$, (e.g., for a start scale parameter (x) and taking into account weightings $\theta$, $\varphi$, $\gamma$ and/or reference data (r), etc. relating to one or more of historical data, performance data, risk, diversity, etc.; etc.). See, again, U.S. Pat. No. 10,327,400 (Title: Methods for Identifying Crosses for use in Plant Breeding), the entire disclosure of which is incorporated herein by reference.

In addition, the data structure 114 in FIG. 1 includes a variety of historical data. In particular, as pertinent herein, the data structure 114 includes historical data testing for a given pipeline or market or decision. That is, where a selection process is performed to select a number of hybrids, for example, the data structure 114 includes the data related to the hybrids that were selected and potentially selected, testing data for the hybrids, and the selection decisions, made by human breeding technicians or other persons, to select or not select the particular hybrid(s). While described with reference to hybrids, it should be appreciated that the data structure 114 may include similar data for other germplasm, such as an origin, progeny, inbred, or other suitable type of plant or biological material (or multiple thereof) exposed to a breeding pipeline, etc.

It should also be appreciated that the germplasm or other plant/biological material in the breeding pipeline 102 may be filtered, by the breeding engine 112, prior to proceeding below. For example, automatically selected plant/biological material may be omitted from the processes below as it is inherently selected based on factors related to its prior plant performance, lineage, diversity, risk, etc. (e.g., as described in U.S. Pat. No. 10,327,400, U.S. Patent Publ. No. 2019/0180845, and U.S. Patent Publ. No. 2019/0174691 the entire disclosures of which are incorporated herein by reference; etc.).

That said, in this example embodiment, the breeding engine 112 is configured to execute Equation (1) with the start set of weights, as noted above, as limited by applicable constraints. The breeding engine 112, in this manner, is configured to select a set of germplasm to be advanced in the pipeline 102. The breeding engine 112 is configured to then compare the selected set of germplasm, via Equation (1), to the reference set of historically selected germplasm from the data structure 114. The percentage of overlap is then set, by the breeding engine 112, as a performance threshold for the start set of weights. For example, where 612 germplasm were selected by Equation (1), while 1,000 were included in the reference set in the data structure 114, the performance of the start set of weights is 0.612 or 61.2 percent.

Next, the breeding engine 112 is configured to iteratively modify the weights. In this example embodiment, the breeding engine 112 is configured to employ either a simulated annealing process or a parallel tempering process. In general, simulated annealing is a stochastic optimization technique that includes a stage of parameter exploration in which a large diversity of parameter configurations can be evaluated, followed by a stage of parameter exploitation in which a small set of the parameter configurations are identified that performed well. This is described in more detail hereinafter. Parallel tempering provides exploration and exploitation stages, by simultaneously executing the stages in parallel chains and allowing the stages to exchange information about the parameter landscape they have discovered, for example, at set intervals. For instance, parallel tempering may provide N copies (or chains) of the weights, randomly initialized at different scale parameters (e.g., different change intensities, or different magnitudes of randomness, or different amplitudes of randomness, etc.). Again, this is described in more detail hereinafter.

In connection with simulated annealing, in this example embodiment, the breeding engine 112 is configured to, for a start scale parameter (e.g., a start value, etc.) in a scale parameter schedule including multiple scale parameters (or scale parameter values) (e.g., at least one scale parameter, at least two scale parameters, at least three scale parameters, at least four scale parameters, more than four scale parameters, at least ten or more scale parameters, at least 50 or scale parameters, etc.) (e.g., a schedule of scale parameters (or scale parameter values) of 50, 20, 8, 5, 2, 1, etc.), modify the start set of weights to provide a first modified set of weights for a first iteration at the start scale parameter (or start scale parameter value). The use of different scale parameters (e.g., in a scale parameter schedule including multiple different scale parameter values, etc.) scales the capability of the parameter search. For example, a larger scale parameter (or scale parameter value) may be associated with a more broadly distributed sampling space from which modified weights may be selected. Likewise, a smaller scale parameter (or scale parameter value) may be associated with a more narrowly distributed sampling space from which the breeding engine 112 may select modified weights. That said, scale parameter values may include, for example, different change intensities, or different magnitudes of randomness, or different amplitudes of randomness, or other suitable values based on the description herein, etc.

The breeding engine 112 is configured to then execute Equation (1) to select a set of germplasm. The breeding engine is configured to then compare the selected set of germplasm to the reference set of germplasm in the data structure 114, as above. When the performance (e.g., the estimated performance, etc.) of the modified set of weights, for the selected set of germplasm, outperforms the start set of weights (e.g., based on percentage of overlap, based on number of overlapping germplasm, etc.), the breeding engine 112 is configured to store the modified set of weights in memory, set the performance threshold to the performance (e.g., the estimated performance, etc.) of the modified set of weights, and proceed to a next iteration. When the performance (e.g., the estimated performance, etc.) of the modified set of weights underperforms the start set of weights, the breeding engine is configured to discard the modified set of weights (or accept the weights when a performance (e.g., the estimated performance, etc.) satisfies a random threshold) and to proceed to a next iteration.

With reference to the above, when the performance (e.g., the estimated performance, etc.) of the modified set of weights underperforms a prior set of weights, the breeding engine 112 is configured to optionally use Equation (2) to calculate an acceptance probability threshold (p) based on a comparison of the performance of the iteration(s) to the performance of the start set of weights, or a prior set of weights. In particular, Equation (2) involves a comparison of the performance value (E') (e.g., estimated performance value, etc.) for the modified set of weights to the performance value (E) (e.g., estimated performance value, etc.) for the start (or prior) set of weights, with reference to the start (or prior) scale parameter (S). The breeding engine 112 is configured to then generate a random value (e.g., between 0 and 1, etc.) and to compare the random value to the acceptance threshold (p) of the new modified set of weights (as defined by Equation (2)). When the random value satisfies the acceptance threshold (e.g., is below the acceptance threshold, is above the acceptance threshold etc.), the breeding engine 112 is configured to accept the new modified weights and set the performance threshold based on the new modified set of weights, prior to advancing to the next iteration. When the random value does not satisfy the acceptance threshold, the breeding engine 112 is configured to discard the new modified set of weights and proceed with the prior set of weights (and corresponding performance threshold) into the next iteration.

$$p = \exp\left(-\frac{E' - E}{S}\right) \quad (2)$$

That said, in this example embodiment, the sequence of modifying the weights, executing Equation (1) and comparing the performance continues until a stop condition is satisfied. The stop condition may include a number of iterations (e.g., at least 50 iterations, at least 100 iterations, at least 500 iterations, at least 1,000 iterations, more than 1,000 iterations, etc.), or potentially, a performance threshold exceeding a stop threshold (e.g., above about 90%, etc.). At the stop condition, the breeding engine 112 is configured to transition to a next scale parameter, if any, in the scale parameter schedule. When the stop condition is satisfied for each scale parameter (or scale parameter value) in the schedule, or another stop condition is satisfied, the breeding engine 112 is configured to automatically identify the set of weights associated with the performance threshold (i.e., the set of weights associated with the best performance for the given scale parameter (or scale parameter value)) as the output weights.

In connection with parallel tempering, in this example embodiment, the breeding engine 112 is configured to initialize the start set of weights into a number of different chains, where each chain is associated with a different scale parameter value in a given scale parameter schedule (or as selected randomly). The breeding engine 112 is configured to then initialize each chain, in parallel, for a desired number of iterations.

For each chain, and iteration thereof, the breeding engine 112 is configured to modify one or more of the weights in the start set. Once modified, the breeding engine 112 is configured to execute Equation (1) and to compare a performance of the modified set of weights to the performance threshold, as described above. When the modified set of weights outperforms, a new performance threshold is set, and when it underperforms, the performance threshold is maintained. When a number of iterations is completed, the set of weights from the last iteration is identified and advanced.

Next, the breeding engine 112 is configured to swap the set of weights for the chain with a set of weights from other ones of the chains, and then to repeat the iterations. The swap exposes certain weights to alteration under a different scale parameter constraint, which is potentially randomly selected (or alternatively associated with the given scale parameter schedule). The breeding engine 112 is configured to then expose the set of weights of each chain, at the new scale parameter value, to further iterations, in parallel (in generally the same manner as described above). After a predefined number of iterations and swaps between chains (e.g., at least about 500 or more, etc.), the breeding engine 112 is configured to identify one or more set of weights, based on the performance threshold for the given chain(s), as described above, as the output weights.

Regardless of the process, the breeding engine 112 is configured to provide the output weights for use with Equation (1) in the specific pipeline (e.g., pipeline 102, etc.) and/or market for which the weights were selected. In this manner, the identified weights are ultimately employed with the algorithm (e.g., Equation (1), etc.) to make decisions about what germplasm (e.g., origins, progenies, hybrids, etc.) to advance within a given breeding pipeline, etc.

Figure 2:
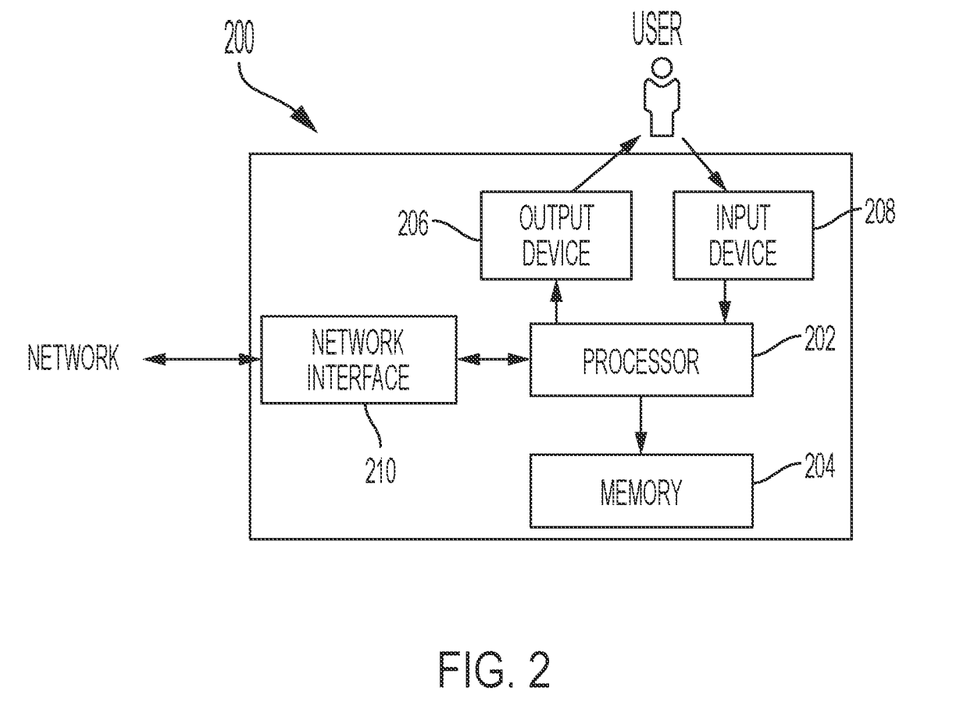
FIG. 2 is a block diagram of a computing device that may be used in the example system of FIG. 1.

FIG. 2 illustrates an example computing device 200 that can be used in the system 100. The computing device 200 may include, for example, one or more servers, workstations, personal computers, laptops, tablets, smartphones, PDAs, terminals, or other suitable physical or virtual machines, etc. In addition, the computing device 200 may include a single computing device, or it may include multiple computing devices located in close proximity or distributed over a geographic region, so long as the computing devices are specifically configured to function as described herein. In the system 100 of FIG. 1, the parent selection and crossing phase 104 and the testing and selection phase 106 of the breeding pipeline 102 are illustrated and described as including, or being implemented in, a computing device 200. In addition, the breeding engine 112 is illustrated and described as including, or being implemented in, a computing device 200. What's more, in various embodiments, the data structure 114 may be included, or may be implemented in, a computing device consistent with computing device 200. That said, the system 100, or parts thereof, should not be understood to be limited to the computing device 200, as other computing devices may be employed in other system embodiments. In addition, different components and/or arrangements of components may be used in other computing devices.

Referring to FIG. 2, the example computing device 200 includes a processor 202 and a memory 204 coupled to (and in communication with) the processor 202. The processor 202 may include one or more processing units (e.g., in a multi-core configuration, etc.). For example, the processor 202 may include, without limitation, a central processing unit (CPU), a microcontroller, a reduced instruction set computer (RISC) processor, an application specific integrated circuit (ASIC), a programmable logic device (PLD), a gate array, and/or any other circuit or processor capable of the functions described herein.

The memory 204, as described herein, is one or more devices that permit data, instructions, etc., to be stored therein and retrieved therefrom. The memory 204 may include one or more computer-readable storage media, such as, without limitation, dynamic random access memory (DRAM), static random access memory (SRAM), read only memory (ROM), erasable programmable read only memory (EPROM), solid state devices, flash drives, CD-ROMs, thumb drives, floppy disks, tapes, hard disks, and/or any other type of volatile or nonvolatile physical or tangible computer-readable storage media. The memory 204 may be configured to store, without limitation, scale parameter data structures (e.g., including scale parameter schedules, etc.), selection algorithms, historical testing data, selection histories, performance data, risk data, diversity data, and/or other types of data (and/or data structures) as needed and/or suitable for use as described herein. Furthermore, in various embodiments, computer-executable instructions may be stored in the memory 204 for execution by the processor 202 to cause the processor 202 to perform one or more of the functions described herein, such that the memory 204 is a physical, tangible, and non-transitory computer readable storage media. Such instructions often improve the efficiencies and/or performance of the processor 202 that is performing one or more of the various operations herein (e.g., one or more of the operations of method 300, method 400, etc.), whereby upon performing of the unique operations provided herein the computing device 200 may be transformed into a special-purpose computing device. It should be appreciated that the memory 204 may include a variety of different memories, each implemented in one or more of the operations or processes described herein.

In the example embodiment, the computing device 200 includes an output device 206 (or presentation unit) that is coupled to (and that is in communication with) the processor 202 (however, it should be appreciated that the computing device 200 could include output devices other than the output device 206, etc.). The output device 206 outputs information (e.g., output sets of weights, performance metrics, etc.), either visually or audibly, to a user of the computing device 200, for example, a user associated with the breeding engine 112, a user associated with one of the phases 104, 106 of the breeding pipeline 102, etc. Various interfaces (e.g., as defined by network-based applications, etc.) may be displayed at computing device 200, and in particular at output device 206, to display such information. The output device 206 may include, without limitation, a liquid crystal display (LCD), a light-emitting diode (LED) display, an organic LED (OLED) display, an "electronic ink" display, speakers, etc. In some embodiments, output device 206 includes multiple devices.

The computing device 200 also includes an input device 208 that receives inputs from the user (i.e., user inputs) such as, for example, selection of a trait of interest, etc., or inputs from other computing devices. The input device 208 is coupled to (and is in communication with) the processor 202 and may include, for example, a keyboard, a pointing device, a touch sensitive panel (e.g., a touch pad or a touch screen, etc.), another computing device, and/or an audio input device. Further, in various example embodiments, a touch screen, such as that included in a tablet, a smartphone, or similar device, behaves as both output device 206 and input device 208.

In addition, the illustrated computing device 200 also includes a network interface 210 coupled to (and in communication with) the processor 202 and the memory 204. The network interface 210 may include, without limitation, a wired network adapter, a wireless network adapter, a mobile network adapter, or other device capable of communicating to/with one or more different computing devices and/or networks. Further, in some example embodiments, the computing device 200 includes the processor 202 and one or more network interfaces incorporated into or with the processor 202.

Figure 3:
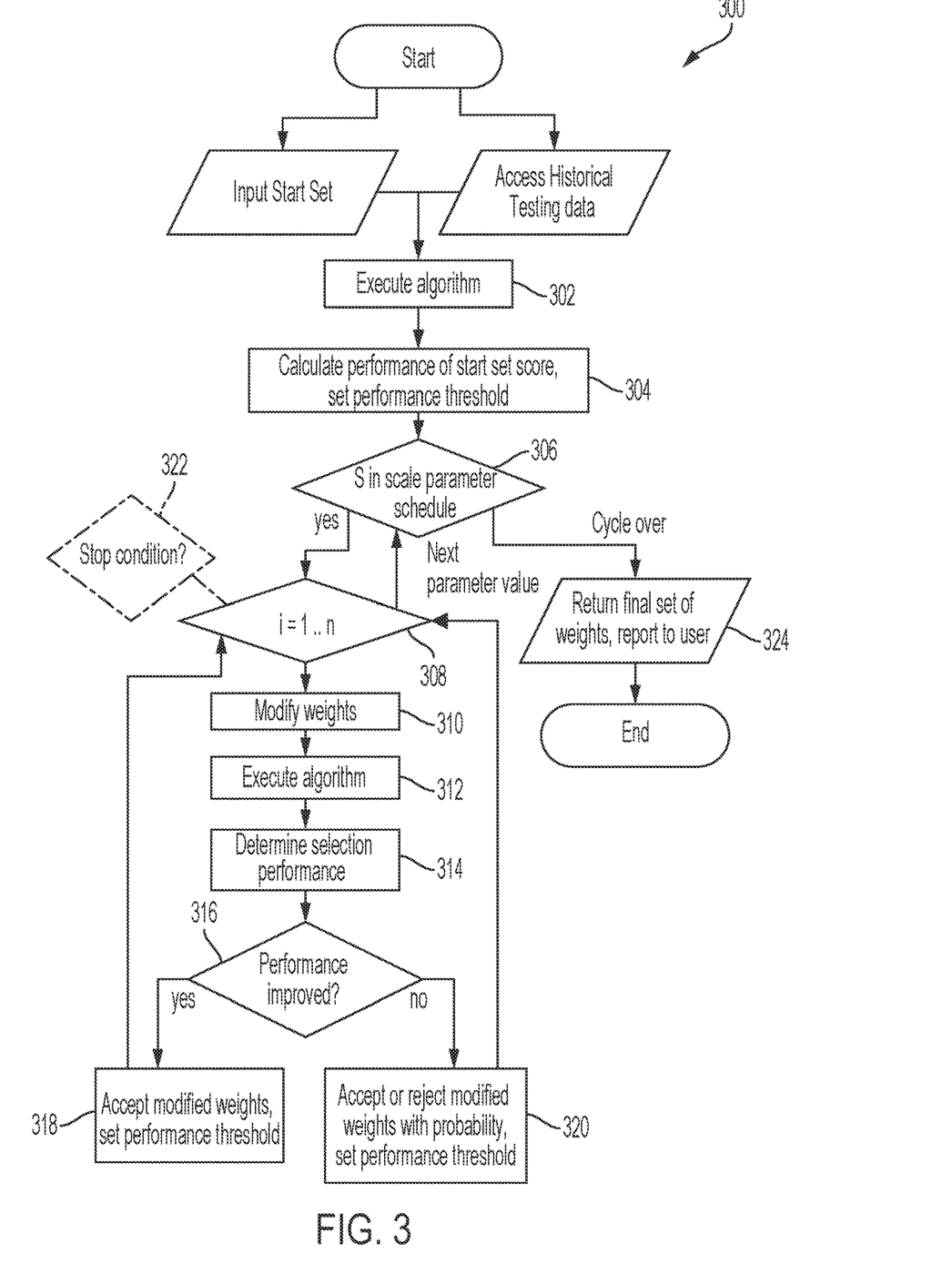
FIG. 3 illustrates an example method, which may be implemented in connection with the system of FIG. 1, for providing identifying weights for use in a selection algorithm (or model)
Figure 4A:
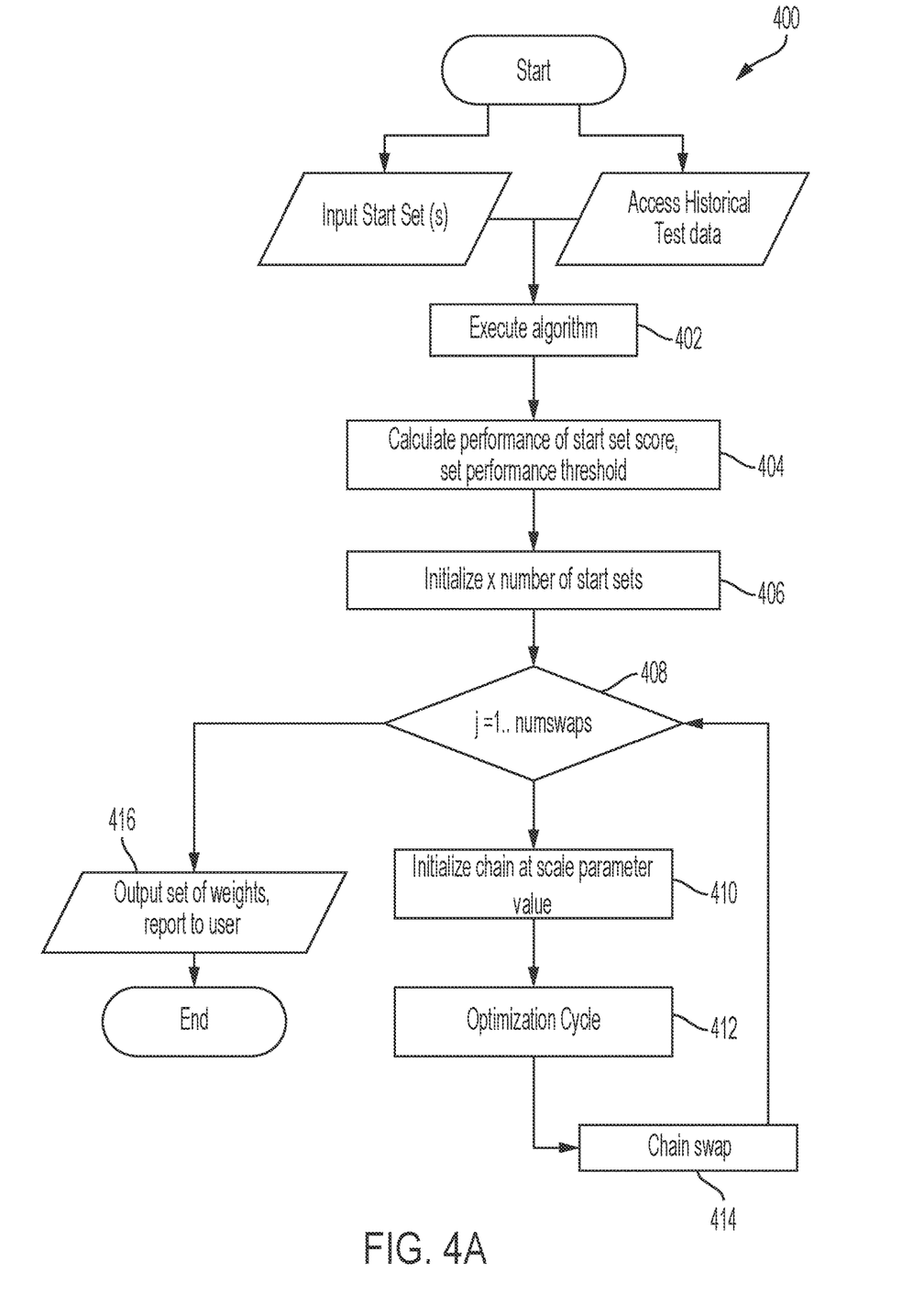
FIGS. 4A-4B illustrate another example method, which may be implemented in connection with the system of FIG. 1, for providing identifying weights for use in a selection algorithm (or model).
Figure 4B:
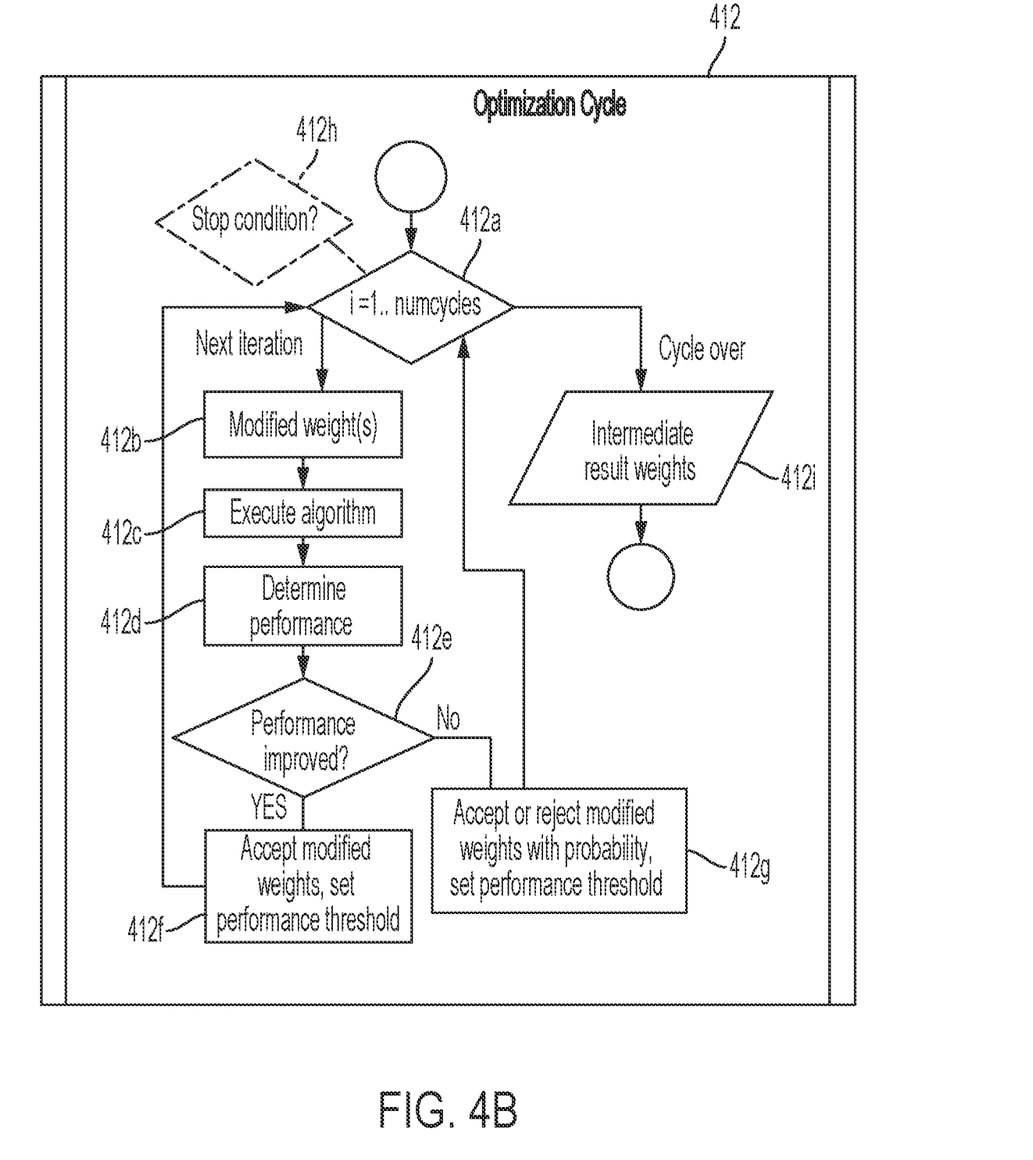

FIGS. 3 and 4 illustrate different example methods 300, 400 for use in automatically identifying weights to be employed in a breeding selection algorithm. Each of the example methods 300, 400 includes modification of a set of weights through an iterative process and a selection of one or more output sets of weights based on performance (e.g., estimated performance, etc.) of the weights in selecting germplasm, for example, consistent with and/or overlapping with a human selection from the same pool of germplasm. Each of the methods 300, 400 is different in the manner and/or interaction among the different iterations, as described in more detail below. Specifically, the method 300 is provided as a simulated annealing process, while the method 400 is provided as a parallel tempering process.

That said, FIG. 3 illustrate example method 300 for use in automatically identifying weights to be employed in a breeding algorithm by way of the simulated annealing process. The method 300 is described below in connection with the example system 100 of FIG. 1 and the example computing device 200 of FIG. 2. However, it should be appreciated that the method 300 is not limited to the system 100 or the computing device 200, but may be implemented in a variety of different systems and/or computing devices. Likewise, the systems and computing devices described herein should not be understood to be limited to the example method 300, or other methods described herein.

As the outset, the method 300 is described with reference to Equation (1) and its use to select a set of germplasm to advance in the breeding pipeline 102. The data structure 114, therefore, includes historical data related to multiple different germplasm, testing data for the germplasm, and a selection or no selection of the germplasm, by a human breeder or other technique, etc. The selection of the germplasm is specific to the pipeline 102 and/or the identified goals for the breeding pipeline 102 (e.g., region, market, disease resistance, stalk strength, etc.) and other considerations specific to the breeding pipeline 102. Given that, in connection with FIG. 3, the method 300 is initiated by accessing a start set of weights for use in Equation (1) (e.g., from a breeding technician, from a prior use of the Equation (1), weights based on empirical testing, etc.) (e.g., potentially a best guess at the proper weights for the breeding engine 112, etc.), whereby the same is available to the breeding engine 112 for use as described below. The start set of weights, as potentially all weights are modified, generally are individually constrained to values between 0 and 1, and the weights together sum to 1 (e.g., $\lambda_p$, $\lambda_r$, $\lambda_{d1}$, $\lambda_{d2}$, and $\lambda_{d3}$=0.2, 0.2, 0.2, 0.2, and 0.2, etc.). These constrains may be different in other embodiments.

Also, the example implementation of the method 300 generally includes accessing the following parameters/data (e.g., from the data structure 114 or from a breeding technician, etc.): a scale parameter schedule for a given/desired scale parameter (e.g., a schedule of scale parameter values, etc.) for simulated annealing: S=(50, 10, 5, 3, 1); a number of iterations (e.g., 100, 200, etc.), and stop conditions, etc. It should be appreciated that these parameters may be different in other embodiments.

As shown in FIG. 3, after accessing the above data, the breeding engine 112 (e.g., computing device 200 as associated therewith, etc.) executes, at 302, Equation (1) with the start set of weights based on the historical data included in the data structure 114. In this manner, the breeding engine 112 selects ones of the germplasm based on a balance of plant performance, risk and diversity of each germplasm, as described in the above incorporated patent and publications. It should be appreciated that the weights impact the importance of risk, for example, over diversity, etc. Once the germplasm are selected, the breeding engine 112 calculates a performance of the start set of weights and stores the performance as a performance threshold, at 304. Here the performance threshold includes the performance of Equation (1), relative to the selection of the human breeders (e.g., percent overlap, number of overlapping germplasm, etc.). For the sake of illustration, the historical test data may include three thousand germplasm, from which 100 were selected by the human breeders (as indicated in the data structure 114). Through operation 302, for example, 100 germplasm may be selected, including 61 of the germplasm selected by the human breeder. As such, in this illustrative example, at 304, the breeding engine 112 calculates an overlap of 0.61 or 61 percent, and sets the performance threshold to 61%.

Next in the method 300, the breeding engine 112 initiates an iterative process for the set of weights. In particular, the breeding engine 112 determines that an iteration for the coding sequence is to be performed and retrieves, at 306, one of the parameter values (S) from the scale parameter schedule in the data structure 114 (e.g., in memory 204, etc.), where the scale parameter values may include 50, 10, 5, 3, 1 (in the same units as performance (e.g., unit-less, units of n-germplasm, etc.) (e.g., based on how the objective(s) associated with the selection of germplasm are defined, etc.)). With a starting scale parameter value of 50, for example, which impacts the available degree of modification of the weights, the breeding engine 112 initiates, at 308, multiple iterations (e.g., iterations (i)=1 to 100, etc.) of modifying the start set of weights for the given scale parameter value selection.

Specifically, to start, the breeding engine 112 initially modifies the start set of weights, at 310. A variety of algorithms may be used to modify the weights, such as, for example, using a random displacement, using a random displacement with adaptive step sizes, etc. In particular, with respect to modifying the weights using random displacement with adaptive step sizes, an adjustment for each weight is calculated by selecting a random displacement value on the interval [−ε, +ε], where ε defines the maximum step size. The random displacement value is then added to the start weight to modify the weight for use in the next iteration. Adaptive sizing of the step size ε avoids overshooting the optima by enabling smaller adjustments of the weights as the optima is approached (e.g., by selecting a smaller step size ε when near the optima). Then, with the modified set of weights, the breeding engine 112 executes, at 312, selection of germplasm via Equation (1) on the historical data included in the data structure 114.

Once the germplasm are selected, the breeding engine 112 determines, at 314, a performance of the modified set of weights. In particular, in this embodiment, as above, the breeding engine 112 determines the overlap between the germplasm selected by Equation (1) with the modified set of weights, relative to the selection of the human breeders. For the sake of illustration, the historical test data may include three thousand germplasm, from which 100 were selected by the human breeder (as indicated in the data structure 114). Through operation 314, for example, 100 germplasm may be selected, including 78 of the germplasm selected by the human breeder. As such, in this illustrative example, at 314, the breeding engine 112 determines the performance of the modified set of weights (for the iteration) to be 0.78 or 78 percent.

Next, the breeding engine 112 determines, at 316, based on the performance threshold and the resulting performance of the modified set of weights for the iteration, if the modified set of weights improves the performance of Equation (1). In this example, because the 78% performance for the modified set of weights is above the 61% performance threshold, the breeding engine determines that the modified set of weights do, indeed, improve the performance of Equation (1). As a result, the modified set of weights is accepted, at 318, by the breeding engine 112, and saved in memory (e.g., the memory 204, etc.). In addition, at 318, the performance of the modified set of weights is set as the performance threshold for the next iteration of the method 300.

Conversely, when the performance of the modified set of weights is below the prior set performance threshold, the breeding engine 112 applies Equation (2) to determine a probability threshold based on the difference in performances (i.e., the iteration performance and the performance threshold) and the scale parameter, and then compares a randomly generated value (e.g., a value between 0 and 1, etc.) to the probability threshold. That said, other equations (other than Equation (2)) may be employed in other embodiments to perform such an analysis. When the random value satisfies the probability threshold, the modified set of weights is accepted, at 320, saved in memory (e.g., the memory 204, etc.), and returned as the input coding sequence for the next iteration (e.g., i=2, etc.). In addition, at 320, the performance of the modified set of weights is set as the performance threshold for the next iteration of the method 300. However, when the probability does not satisfy the random threshold, the new coding sequence is rejected, at 320, and the prior set of weights is reused to start the next iteration (e.g., i=2, etc.). In this manner, a lower score set of weights has the opportunity to advance for the next iteration, thereby providing for further flexibility in the method 300.

When each of the iterations is complete (e.g., when i=100 in the illustrated embodiment, etc.), the breeding engine 112 identifies and stores the output set of weights in memory (e.g., the memory 204, etc.). The breeding engine 112 then returns, as indicated in FIG. 3, to step 306 and proceeds with the next scale parameter value (e.g., the next N-th scale parameter value, etc.) in the data structure (including the scale parameter schedule) (e.g., 50, 10, 3, 1, etc.). At the next scale parameter value in the data structure, the breeding engine 112 proceeds consistent with the above description of steps 308-320.

In addition to the iteration limit and the scale parameter schedule, the breeding engine 112 optionally (as indicated by the broken lines in FIG. 4B) employs one or more different stop conditions, at 322. Specifically, for example, a breeding technician may impose a stop condition (e.g., an early stop condition) based on performance, such as, a performance above 90%. As such, at 322, when the performance for a last modified set of weights exceeds 90%, the breeding engine 112 may optionally stop the iterative processes, and proceed to step 324, described below. Other example stop conditions may include a degree of performance increase over a number of iterations (e.g., less than 3% increase over twenty iterations, etc.). Otherwise, if no stop conditions are satisfied (or employed), steps 308-320 are repeated until the iteration limit is reached for the final scale parameter value, i.e., the N-th scale parameter value, of the scale parameter schedule.

Apart from the stop conditions, when the steps 308-320 are repeated and completed for the final scale parameter value, i.e., the N-th scale parameter value, the breeding engine 112 generates and returns a report, at 324, which includes the final set of weights and corresponding performance, etc. The breeding engine 112 may return the report to a breeding technician or other user associated with the method 300 and/or store the report in memory (e.g., the memory 204 associated with the breeding engine 112, etc.). Thereafter, the method 300 ends, and the breeding technician, or other user, may implement one or multiple of the final set of weights in the Equation (1) for selection of a next generation of germplasm in the breeding pipeline 102 of FIG. 1.

FIGS. 4A-4B illustrate another example method 400 for use in automatically identifying weights to be employed in a breeding algorithm, this time by way of the parallel tempering process. The method 400 is described in connection with the example system 100 of FIG. 1 and the example computing device 200 of FIG. 2. However, it should be appreciated that the method 400 is not limited to the system 100 or the computing device 200, but may be implemented in a variety of different systems and/or computing devices. Likewise, the systems and computing devices described herein should not be understood to be limited to the example method 400, or other methods described herein.

Like method 300, method 400 is subject to certain parameters, such as, for example, scale parameters as included in one or more scale parameter schedules (e.g., schedules including values such as 50, 10, 3, 1, etc. relating to different change intensities, or different magnitudes of randomness, or different amplitudes of randomness, etc.; etc.); other parameter schedules including similar values or different values; etc.), a number of iterations between swaps (e.g., 25, 50, 100, 500, 1,000, etc.), a number of swaps (e.g., 50, 100, 500, 1,000, etc.), a number of chains (e.g., four chains or more or less, etc.), etc.

At the outset in the method 400, the breeding engine 112 (e.g., computing device 200 as associated therewith, etc.) accesses/receives a start set of weights (e.g., from a breeding technician, from a prior use of the Equation (1), weights based on empirical testing, etc.) (e.g., potentially a best guess at the proper weights for the breeding engine 112, etc.) and accesses the historical testing data in the data structure 114. And, the breeding engine 112 executes, at 402, Equation (1), with the start set of weights, on the historical data included in the data structure 114. In this manner, the breeding engine 112 selects ones of the germplasm based on a balance of plant performance, risk and diversity for each germplasm, as described in the above incorporated patent and publications. It should be appreciated that the weights impact the importance of risk, for example, over diversity, etc. Once the germplasm are selected, the breeding engine 112 calculates a performance of the start set of weights and stores the performance as a performance threshold, at 404. Here the performance threshold includes the performance of Equation (1), relative to the selection of the human breeders (e.g., a percentage overlap, a number of overlapping germplasm, etc.). For the sake of illustration again, the historical test data may include three thousand germplasm, from which 100 were selected by the human breeder (as indicated in the data structure 114). Through operation 402, for example, 100 germplasm may be selected, including 61 of the germplasm selected by the human breeder. As such, in this illustrative example, at 404, the breeding engine 112 calculates an overlap of 0.61 or 61 percent, and sets the performance threshold to 61%.

Next in the method 400, the breeding engine 112 initiates, at 406, X-number of copies of the start set of weights (e.g., based on a number (N) of scale parameter values in the scale parameter schedule, etc.). Once initialized, the breeding engine 112 assigns, at 408, each of the start sets to one of the branches of the swap loop, along with the corresponding scale parameter value. Thereafter, each of the chains is initialized, individually and in parallel, at 410, at specific scale parameter values, as assigned to the different chains. In one example, each scale parameter value in the scale parameter scheduled is assigned to a chain (i.e., five scale parameter values and five chains, etc.). Again, as mentioned above, the scale parameter value of the given chain provides for the freedom to modify the set of weights in the specific iterations (e.g., a lower scale parameter value may provide a smaller modification to the set of weights per iteration, while a higher scale parameter value may provide a greater modification to the set of weights per iteration).

Thereafter, for each branch, the breeding engine 112 runs an optimization cycle for the coding sequence and corresponding scale parameter value of the branch, at 412. FIG. 4B illustrates a sub-process for the optimization cycle (step 412), for the given branch. In this example embodiment, the breeding engine 112 enters twenty-five iterations, at 412a, for each optimization cycle for each branch (i.e., i=1, i=2, . . . i=25), but may enter a different number of iterations in other method embodiments (e.g., 15, 50, 100, etc.).

For the first iteration, the breeding engine 112 modifies the start set of weights, at 412b, based on the start set of weights, for example, using a random displacement with an adaptive step size, as described above. And, the breeding engine 112 then executes, at 412c, selection of germplasm via Equation (1), with the modified set of weights, on the historical data included in the data structure 114.

Once the germplasm are selected, the breeding engine 112 determines, at 412d, a performance of the modified set of weights. In particular, in this embodiment, as above, the breeding engine 112 determines the overlap between the germplasm selected by Equation (1) with the modified set of weights, relative to the selection of the human breeders as provided in the data structure 114. For the sake of illustration, the historical test data may include three thousand germplasm, from which 100 were selected by the human breeder (as indicated in the data structure 114). Through operation 412c, for example, 100 germplasm may be selected, including 78 of the germplasm selected by the human breeder. As such, in this illustrative example, at 412d, the breeding engine 112 determines the performance of the modified set of weights (for the iteration) to be 0.78 or 78 percent.

Next, the breeding engine 112 determines, at 412e, based on the performance threshold and the performance of the modified set of weights for the iteration, whether the modified set of weights improves the performance of Equation (1) over the start weights. Again, in this example, because 78% performance is above the prior performance threshold (as determined at 404), the breeding engine 112 determines that the modified set of weights do, indeed, improve the performance of Equation (1). As a result, the modified set of weights is accepted, at 412f, by the breeding engine 112, and saved in memory (e.g., the memory 204, etc.). In addition, at 412f, the performance of the modified set of weights is set as the performance threshold for the next iteration of the cycle, at 412.

Conversely, when the performance of the modified set of weights is below the performance threshold, the breeding engine 112 applies Equation (2) above to determine a probability threshold based on the difference in performances (i.e., the iteration performance and the performance threshold) and the scale parameter value, and then compares a randomly generated value (e.g., a value between 0 and 1, etc.) to the probability threshold. That said, other equations (other than Equation (2)) may be employed in other embodiments to perform such an analysis. When the random value satisfies the probability threshold, the modified set of weights is accepted, at 412g, saved in memory (e.g., the memory 204, etc.), and returned as the input coding sequence for the next iteration (e.g., i=2, etc.). In addition, at 412g, the performance of the modified set of weights is set of as the performance threshold for the next iteration of the operation 412 of method 400. Conversely, when the random value does not satisfy the probability threshold, the new coding sequence is rejected, at 412g, and the prior set of weights is reused to start the next iteration (e.g., i=2, etc.). In this manner, a lower score set of weights has the opportunity to advance for the next iteration, thereby providing for further flexibility in the method 400.

When each of the iterations is complete (e.g., when i=25 in the illustrated embodiment, etc.), the optimization phase (or cycle), at 412, is complete. In addition to the iteration limit, the breeding engine 112 optionally employs (as indicated by the broken lines in FIG. 4B), as part of the optimization phase (or cycle), one or more different stop conditions (e.g., prior to reaching the iteration limit), at 412h, to stop the optimization phase, such that the phase is complete. A stop condition may be based on performance, such as, a performance above 90%, a degree of performance increase over a number of iterations (e.g., less than 3% increase over twenty iterations, etc.), etc. Thereafter, the breeding engine 112 identifies and stores, at 412i, an intermediate set of weights in memory (e.g., the memory 204, etc.). The operation of the breeding engine 112 then returns to FIG. 4A.

In connection therewith, the breeding engine 112 enters a chain swap, at 414. As part of the chain swap, the breeding engine 112 exchanges the intermediate set of weights among the different branches, whereby each set of weights from one scale parameter value is exposed to an optimization cycle at a different scale parameter value. In particular, the breeding engine 112 attempts, for example, to assign the higher performing weights to lower scale parameter values, while assigning the lower performing weights to higher scale parameter values (e.g., depending on the given scale parameter (e.g., depending on different change intensities, or different magnitudes of randomness, or different amplitudes of randomness, etc.). The higher scale parameter values, accordingly, may permit more variability and flexibility whereby the worse performing weights are eligible for greater change (e.g., to search more weights, etc.), while the better performing weights are exposed to lower scale parameter values which may permit less variability (e.g., to provide refinement, etc.). Based on performance and scale parameter value of the chains, chain swaps may occur either with certainty or with probability. For example, if weights assigned to a higher scale parameter value chain have better performance than weights assigned to a lower scale parameter value chain, then the chains are automatically swapped with certainty. If, however, weights assigned to a higher scale parameter value chain underperform weights assigned to a lower scale parameter value chain, then the chains are swapped, or not, with probability as defined in Equation (3).

$$P = \exp\left(\frac{E_{higher} - E_{lower}}{\frac{1}{S_{higher}} - \frac{1}{S_{lower}}}\right) \quad (3)$$

Once the swap of the intermediate sets of weights is complete, the breeding engine 112 returns to operation 408, whereby the breeding engine 112 increments the swap counter (j) from 1 to 2, for example, and proceeds as described above. The breeding engine 112 will continue in method 400 until a number of swaps reaches a predefined maximum (e.g., 100, 400, etc.) or the algorithm reaches a stopping condition, as described above. It should be appreciated that various stop conditions may exist, as defined, for example, by a breeder technician or another user associated with the method 400 or the specific desires associated with the expression to be enhanced through method 400 (i.e., performance).

Finally in the method 400, once the swap conditions are completed, the breeding engine 112 generates and returns a report, at 416, which includes the final set of weights and corresponding performance for the final set of weights, etc. The breeding engine 112 may return the report to a breeding technician or other user associated with the method 400 and/or store the report in memory (e.g., the memory 204 associated with the breeding engine 112, etc.). Thereafter, the method 400 ends, and the breeding technician or other user may implement one or multiple of the final set of weights in the Equation (1) for selection of a next generation of germplasm in the breeding pipeline 102 of FIG. 1.

Through the present disclosure, parents (e.g., germplasm associated therewith, etc.) may be automatically selected for use in breeding pipelines (e.g., identified, etc.) based on weighted values associated with different characteristics of the parents (e.g., predicted commercial values of potential crosses between the parents, relatedness and/or risks associated with the given crosses, individual traits and/or characteristics of the parents (and/or the parents' parents, and/or other members in the parental lines), etc.). In connection therewith, then, plants may be grown (or derived) (e.g., in growing spaces of the breeding pipelines (e.g., as part of one or more breeding programs, etc.), etc.) from the selected parents. As such, the plants may be part of the breeding pipelines (e.g., part of the breeding pipeline 102, etc.) and the systems including the same (e.g., the system 100, etc.). What's more, through the application of the weighted values in identifying the selected parents, the plants grown therefore are more likely to yield commercial products (e.g., through use of, evaluation of, etc. smaller numbers of parents; etc.).

In view of the above, the systems and methods herein provide for the selection of parents for use in breeding pipelines based on weighted values associated with predicted commercial values of potential crosses between the parents, relatedness and/or risks associated with the given crosses, and individual traits and/or characteristics of the parents (and/or the parents' parents, and/or other members in the parental lines). For example, rather than relying on manual formulation of the weighting between the different parameters, the systems and methods herein automatically select the weighting based on identified overlap between the selected parents and parents selected by human breeders, or by other manners of identifying selected parents as correct and/or preferred, whereby enhanced decision making is provided based on such selections. In this manner, a more complete picture of the potential crosses of the parents is provided, from which efficiency in selecting populations of crosses for the plant breeding pipelines can be gained.

Again, and as previously described, it should be appreciated that the functions described herein, in some embodiments, may be described in computer executable instructions stored on a computer readable media, and executable by one or more processors. The computer readable media is a non-transitory computer readable storage medium. By way of example, and not limitation, such computer-readable media can include RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Combinations of the above should also be included within the scope of computer-readable media.

It should also be appreciated that one or more aspects of the present disclosure transform a general-purpose computing device into a special-purpose computing device when configured to perform the functions, methods, and/or processes described herein.

As will be appreciated based on the foregoing specification, the above-described embodiments of the disclosure may be implemented using computer programming or engineering techniques including computer software, firmware, hardware or any combination or subset thereof, wherein the technical effect may be achieved by performing at least one of the following operations: (a) identifying (i) a start set of weights for a selection algorithm associated with a breeding program and (ii) a start set of germplasm based on historical test data, the start set of germplasm associated with a performance threshold; (b) for each scale parameter value in a scale parameter schedule, and for each of N iterations, where N is an integer: (A) modifying the start set of weights based on the scale parameter value; (B) identifying a set of germplasm based on the selection algorithm, the modified set of weights, and the scale parameter value; (C) advancing the modified set of weights to a next iteration as the start set of weights, in response to (i) an estimated performance of the identified set of germplasm satisfying the performance threshold and (ii) the iteration being less than N; and (D) identifying the modified set of weights as an output for the N iterations in response to (i) the estimated performance of the identified set of germplasm satisfying the performance threshold and (ii) the iteration being equal to N; and (c) returning one of the outputs, for one of the scale parameter values in the scale parameter schedule, as a final set of weights for the selection algorithm associated with the breeding program.

As will also be appreciated based on the foregoing specification, the above-described embodiments of the disclosure may be implemented using computer programming or engineering techniques including computer software, firmware, hardware or any combination or subset thereof, wherein the technical effect may be achieved by performing at least one of the following operations: (a) identifying a start set of weights for a selection algorithm associated with a breeding program as an input for each of M chains, the start set of weights associated with a performance threshold; (b) for each of the M chains, where M is an integer, initializing N iteration(s) for the start set of weights for the chain at one of multiple defined scale parameter values, where N is an integer; and (c) for each of the N iterations: (i) modifying the start set of weights based on a scale parameter value of the chain; (ii) identifying a set of germplasm based on the selection algorithm, the modified set of weights, and the scale parameter value; (iii) advancing the modified set of weights to a next iteration as the start set of weights, in response to (A) an estimated performance of the identified set of germplasm satisfying the performance threshold, (B) the estimated performance of the identified set of germplasm satisfying a further threshold, and (C) the iteration being less than N; and (iv) identifying the modified set of weights as an output for the N iterations in response to (A) the estimated performance of the identified set of germplasm satisfying the performance threshold and (C) the iteration being equal to N; (iv) after the N iterations, for each of the M chains, swapping the output of said M chain with the output of a different one of the M chains; (v) initializing another N iteration(s) for the output as the start set of weights at one of multiple defined scale parameter values and, for each of the another N iteration(s), repeating operations (a) through (d); and (vi) after the output is swapped among the M chains X times, identifying at least one of the outputs as a final set of weights for the selection algorithm associated with the breeding program.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail (but this does not mean the subject matcher recited in the claims is well-known).

Specific values disclosed herein are example in nature and do not limit the scope of the present disclosure. The disclosure herein of particular values and particular ranges of values for given parameters are not exclusive of other values and ranges of values that may be useful in one or more of the examples disclosed herein. Moreover, it is envisioned that any two particular values for a specific parameter stated herein may define the endpoints of a range of values that may be suitable for the given parameter (i.e., the disclosure of a first value and a second value for a given parameter can be interpreted as disclosing that any value between the first and second values could also be employed for the given parameter). For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When a feature is referred to as being "on," "engaged to," "connected to," "coupled to," "associated with," "in communication with," or "included with" another element or layer, it may be directly on, engaged, connected or coupled to, or associated or in communication or included with the other feature, or intervening features may be present. As used herein, the term "and/or" and the phrase "at least one of" include any and all combinations of one or more of the associated listed items.

Although the terms first, second, third, etc. may be used herein to describe various features, these features should not be limited by these terms. These terms may be only used to distinguish one feature from another. Terms such as "first," "second," and other numerical terms when used herein do not imply a sequence or order unless clearly indicated by the context. Thus, a first feature discussed herein could be termed a second feature without departing from the teachings of the example embodiments.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for use in identifying weights to be employed in a selection algorithm associated with plant advancement, the system comprising:
a computing device configured to:
identify a start set of weights for a selection algorithm associated with a breeding program and a start set of germplasm defined by the selection algorithm and the start set of weights, the start set of germplasm associated with a performance threshold;
for each scale parameter value in a scale parameter schedule:
for each of N iterations, where N is an integer:
modify the start set of weights based on the scale parameter value;
identify a set of germplasm based on the selection algorithm, the modified set of weights, and the scale parameter value;
advance the modified set of weights to a next iteration as the start set of weights, in response to i) an estimated performance of the identified set of germplasm satisfying the performance threshold and ii) the iteration being less than N;
advance the modified set of weights to a next iteration as the start set of weights, in response to i) the estimated performance of the identified set of germplasm failing to satisfy the performance threshold, ii) the estimated performance of the identified set of germplasm satisfying a further threshold, and iii) the iteration being less than N; and
identify the modified set of weights as an output for the N iterations in response to i) the estimated performance of the identified set of germplasm satisfying the performance threshold and ii) the iteration being equal to N; and
return one of the outputs, for one of the scale parameter values in the scale parameter schedule, as a final set of weights for the selection algorithm associated with the breeding program.

2. The system of claim 1, wherein the computing device is configured to randomly modify the start set of weights consistent with the scale parameter value.

3. The system of claim 1, wherein the scale parameter schedule includes multiple scale parameter values, and wherein each of the scale parameter values is indicative of variability available for modifying the set of weights.

4. The system of claim 1, wherein the computing device is configured to identify the set of germplasm based on historical test data, via the selection algorithm.

5. The system of claim 1, wherein the computing device is further configured, for each scale parameter value in the scale parameter schedule, and for each of the N iterations, to calculate the estimated performance of the set of germplasm as a percentage overlap between the set of germplasm and a reference set of germplasm, and to compare the estimated, calculated performance to the performance threshold.

6. The system of claim 5, wherein the computing device is further configured, for each scale parameter value in the scale parameter schedule, and for each of the N iterations, to identify the modified set of weights as an output for the N iterations in response to a stop condition being satisfied.

7. The system of claim 6, wherein the stop condition includes at least one of: the estimated performance of the modified set of germplasm exceeding a threshold and/or a degree of performance increase over a number of iterations.

8. The system of claim 1, wherein the computing device, in connection with advancing the modified set of weights to a next iteration as the start set of weights, is configured to set the estimated performance of the identified set of germplasm as the performance threshold.

9. The system of claim 1, wherein the computing device is further configured, in response to the estimated performance of the identified set of germplasm failing to satisfy the performance threshold and the iteration being less than N, to:
calculate the further threshold as an acceptance probability threshold for the estimated performance of the identified set of germplasm based on:

$$p = \exp\left(-\frac{E' - E}{S}\right),$$

wherein E' is the estimated performance of the identified set of germplasm, E is the performance threshold, and S is the scale parameter value;
compare the acceptance probability to a randomly generated number for the scale parameter value and the N iteration; and
determine the further threshold is satisfied in response to the randomly generated number satisfying the acceptance probability.

10. The system of claim 1, wherein the computing device is further configured, for each scale parameter value in the scale parameter schedule, for each of the N iterations, to:
discard the modified set of weights; and
advance the start set of weights to a next iteration as the start set of weights, in response to i) the estimated performance of the identified set of germplasm failing to satisfy the performance threshold, ii) the estimated performance of the identified set of germplasm failing to satisfy the further threshold, and iii) the iteration being less than N.

11. The system of claim 1, wherein N is less than 500.

12. The system of claim 1, wherein the computing device is further configured to identify at least one germplasm based on the final set of weights and the selection algorithm.

13. The system of claim 12, further comprising a plant disposed in a growing space of a breeding pipeline of the breeding program, the plant derived from the at least one germplasm.

14. The system of claim 1, wherein the computing device is further configured to generate a report of the final set of weights and the estimated performance associated with the final set of weights.

15. A method for use in identifying weights to be employed in a selection algorithm associated with plant advancement, the method comprising:
identifying i) a start set of weights for a selection algorithm associated with a breeding program and ii) a start set of germplasm based on historical test data, the start set of germplasm associated with a performance threshold;
for each scale parameter value in a scale parameter schedule:
for each of N iterations, where N is an integer:
modifying the start set of weights based on the scale parameter value;
identifying a set of germplasm based on the selection algorithm, the modified set of weights, and the scale parameter value;
advancing the modified set of weights to a next iteration as the start set of weights, in response to i) an estimated performance of the identified set of germplasm satisfying the performance threshold and ii) the iteration being less than N; and
identifying the modified set of weights as an output for the N iterations in response to i) the estimated performance of the identified set of germplasm satisfying the performance threshold and ii) the iteration being equal to N; and
returning one of the outputs, for one of the scale parameter values in the scale parameter schedule, as a final set of weights for the selection algorithm associated with the breeding program.

16. The method of claim 15, wherein modifying the start set of weights includes randomly modifying the start set of weights consistent with the scale parameter value; and
wherein the scale parameter schedule includes multiple scale parameter values, and wherein each of the scale parameter values is indicative of variability available for modifying the set of weights.

17. The method of claim 15, further comprising, for each scale parameter value in the scale parameter schedule, and for each of the N iterations:
calculating the estimated performance of the set of germplasm as a percentage overlap between the set of germplasm and a reference set of germplasm; and
comparing the estimated, calculated performance to the performance threshold.

18. The method of claim 17, further comprising, in response to the estimated performance of the identified set of germplasm failing to satisfy the performance threshold and the iteration being less than N:
calculating the further threshold as an acceptance probability threshold for the estimated performance of the identified set of germplasm based on:

$$p = \exp\left(-\frac{E' - E}{S}\right),$$

wherein E' is the estimated performance of the identified set of germplasm, E is the performance threshold, and S is the scale parameter value;
comparing the acceptance probability to a randomly generated number for the scale parameter value and the N iteration; and
determining the further threshold is satisfied in response to the randomly generated number satisfying the acceptance probability.

19. The method of claim 15, wherein N is less than 500.

20. The method of claim 15, further comprising planting a plant in a growing space of a breeding pipeline of the breeding program, the plant derived from the at least one germplasm.

* * * * *